United States Patent [19]

MacGregor

[11] Patent Number: 4,712,553
[45] Date of Patent: Dec. 15, 1987

[54] SUTURES HAVING A POROUS SURFACE

[75] Inventor: David C. MacGregor, Miami, Fla.

[73] Assignee: Cordis Corporation, Miami, Fla.

[21] Appl. No.: 739,545

[22] Filed: May 30, 1985

[51] Int. Cl.[4] ............................ A61F 2/00; A61L 17/00
[52] U.S. Cl. ................................... 128/335.5; 623/11; 623/13; 623/66
[58] Field of Search ............... 128/334 R, 335.5, 335, 128/339; 623/11, 12, 66, 1, 13

[56] References Cited

U.S. PATENT DOCUMENTS

| | | | |
|---|---|---|---|
| 1,337,480 | 4/1920 | Matthaei | 128/339 |
| 2,940,247 | 6/1960 | Kirschbaum | 128/335.5 |
| 3,094,123 | 6/1963 | Kurtz | 128/339 |
| 3,130,728 | 4/1964 | Pearson | 128/335.5 |
| 3,187,752 | 6/1965 | Glick | 128/335.5 |
| 3,317,924 | 5/1967 | Le Veen . | |
| 3,791,288 | 2/1974 | Hunter | 128/335.5 |
| 3,847,156 | 11/1974 | Trumble | 128/335.5 |
| 3,953,566 | 4/1976 | Gore . | |
| 3,992,725 | 11/1976 | Homsy . | |
| 4,043,344 | 8/1977 | Landi | 128/335.5 |
| 4,044,404 | 8/1977 | Martin et al. | 623/1 |
| 4,096,227 | 6/1978 | Gore . | |
| 4,101,984 | 7/1978 | MacGregor . | |
| 4,110,392 | 8/1978 | Yamazaki . | |
| 4,116,738 | 9/1978 | Pall . | |
| 4,173,689 | 11/1979 | Lyman et al. . | |
| 4,355,426 | 10/1982 | MacGregor . | |
| 4,385,093 | 5/1983 | Hubis . | |
| 4,459,252 | 7/1984 | MacGregor . | |
| 4,475,972 | 10/1984 | Wong . | |

OTHER PUBLICATIONS

Leidner et al, "A Novel Process for the Manufacturing of Porous Grafts: Process Description and Product Evaluation," *Journal of Biomedical Materials Research*, vol. 17, pp. 229–247.

W. L. Gore and Associates, Inc., *Investigating Surgeons Brochure Gore-Tex Expanded PTFE Suture.*

Primary Examiner—Richard J. Apley
Assistant Examiner—Alan W. Cannon
Attorney, Agent, or Firm—Lockwood, Alex, FitzGibbon & Cummings

[57] ABSTRACT

Surgical sutures are provided that have a surface which has a porous structure. The porous structure can be formed from a plurality of fibers that are wound onto an elongated central core of the suture, or from a mixture including elutable particles that is cast into the configuration of a suture, either as a generally unitary cylinder or over an elongated central core of the suture.

13 Claims, 13 Drawing Figures

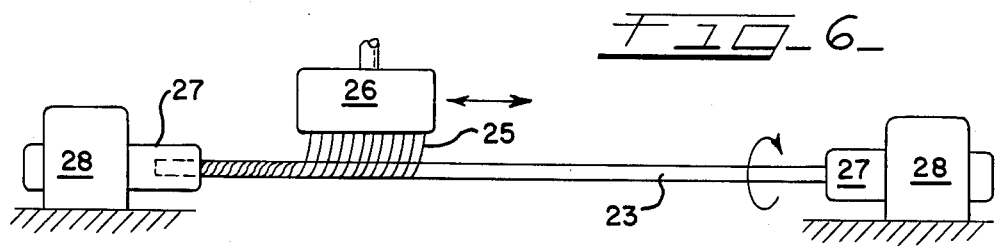
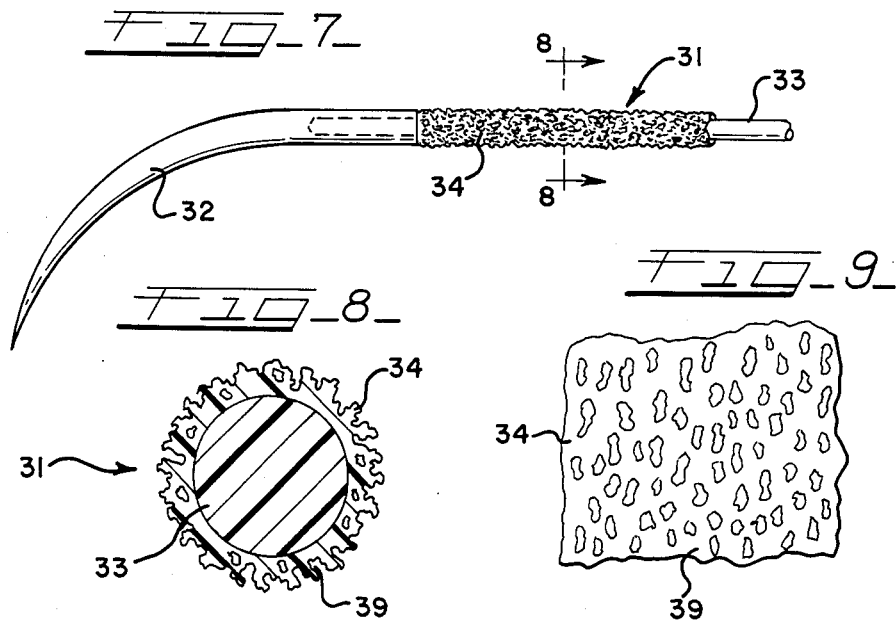
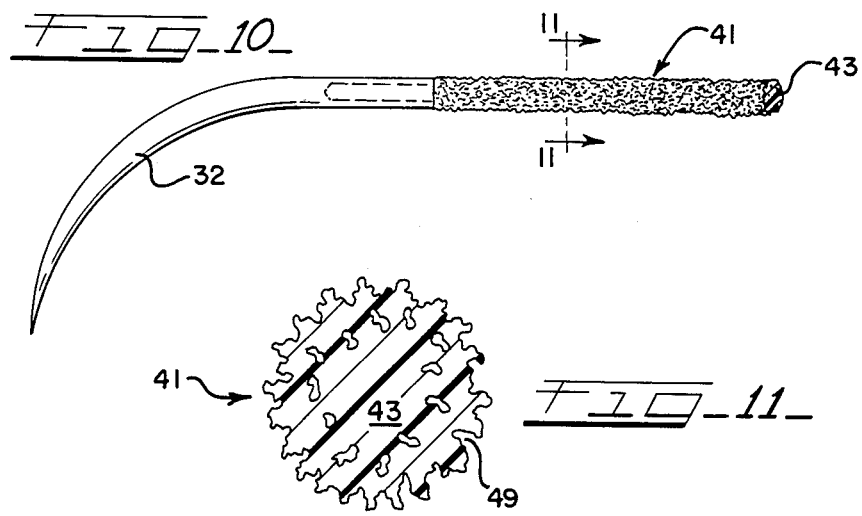

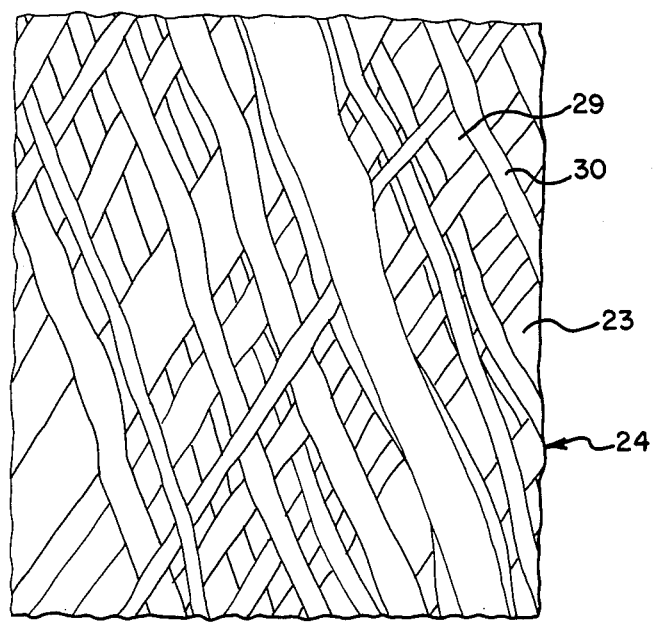
FIG_12_
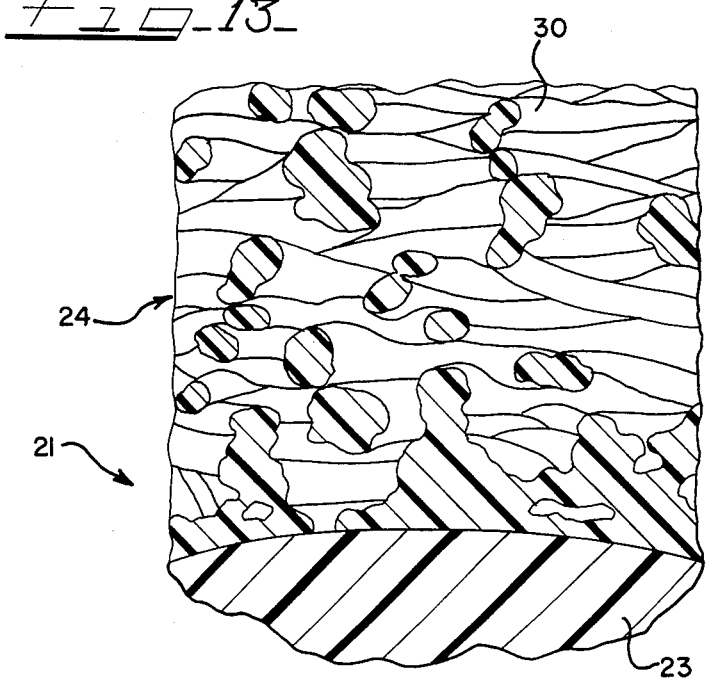
FIG_13_

SUTURES HAVING A POROUS SURFACE

BACKGROUND AND DESCRIPTION OF THE INVENTION

The present invention generally relates to surgical sutures having a surface which has a porous structure, the suture being of the non-braided and non-woven type and having a surface porosity that provides an environment that is conducive to tissue ingrowth into the pores of the porous surface. The porous surface may be formed from a plurality of fibers that are wound onto an elongated filament and onto themselves while providing adequate spacing therebetween so as to form a surface having pores of the desired size. Alternatively, the porous surface can be formed from a mixture of polymer and salt elutable particles, which mixture is cast into the configuration of a suture, after which the salt elutable particles are eluted in order to form the porous surface of the suture.

Most sutures which are available today for the repair, fixation and/or approximation of body tissues during surgical procedures are composed of single strands or multiply braided strands of flexible material, with or without a needle attached to one or both ends of the flexible material. Sutures which are used for the attachment of prosthetic devices or implants to body tissues have especially stringent requirements regarding strength, biocompatibility, flexibility, sterilizability and, in some cases, biodegradability. An especially desirable property for sutures that are intended for specialized uses such as those involving biologic, synthetic or biosynthetic vascular grafts is to provide the suture with porosity that extends to the external surface of the suture and that provides for rapid tissue ingrowth and endothelialization, as well as other important properties.

Providing prosthetic devices and implants with porous surfaces has been developed during the last few years in order to promote the implantation of such devices. Porous coatings or surfaces have been implemented on or proposed in connection with devices such as heart valves, cardiac pacers and electrodes thereof, vascular grafts, blood pumps, ventricular assist devices, artificial hearts, flexible heart valve members, bloodstream filters, intracardiac patches, diaphragms or baffles, vascular access tubes, and the like. One of the objectives of providing porous surfaces on these types of devices and implants is to promote colonization and tissue ingrowth into the depth of the porous surface from adjacent body tissue in order to provide bonding between the body tissue host and the porous member. Typically, the body tissue ingrowth is combined with the promotion of tissue growth into the porous surface from the nucleated bloodstream cells. Such porous surfaces provide a porous depth that affords a means of fixation to host tissues by soft tissue growth into the porous depth of the surface, and they provide tissue-implant interfaces which are blood compatible arising from colonization and tissue formation on the blood-contacting surfaces.

Imparting porosity to sutures according to the present invention has been found to provide advantageous results including permitting body tissue ingrowth into the pores of the suture in order to accelerate the healing process. By allowing tissue ingrowth into the interstices of the porous suture, potential dead spaces are reduced or eliminated thus making the suture less prone to primary or secondary infection. The porous suture also provides the possibility for reduced intimal hyperplasia and stenotic narrowing at the anastomotic site. The generally compressible nature of the porous suture permits the use of a needle whose diameter is less than that of the suture itself in order to thereby reduce blood leakage at suture sites in vascular anastomoses.

Additionally, surface irregularities that are associated with the porous suture structure according to this invention result in less slippage when the suture is tied in order to provide a more secure knot than that achieved by using smooth or monofilament sutures. The porous suture structure also provides a favored environment for the controlled release of drugs to promote healing and/or to resist infection. Porous sutures according to this invention can be made of the same material as, and be provided with a surface structure that is similar to, the device being implanted with the aid of the suture, such as a synthetic graft, with the result that the suture material will demonstrate substantially the same physical and chemical properties as the device being sutured. This can be of assistance in promoting more uniform healing because the surface free energy of the porous suture will be similar to that of the graft being secured thereby. If desirable, the porous suture can be bonded to the vascular graft or the like, which is facilitated when the suture and the graft are made of substantially the same material.

These various properties and advantages have been attained by the present invention, by which a non-braided surgical suture is provided which includes an exterior portion having a porous structure, such exterior portion being between the outer surface of the suture and a location internal thereof to provide a porous surface or layer. The porous surface or layer may be formed by winding spun fibers or by salt elution techniques. This porous surface or layer may be formed over a generally continuous elongated core member by the winding or the elution procedure, or it may be formed by salt elution from a continuous elongated polymeric member. In any case, the suture, including its porous surface or layer, is constructed of a polymeric material.

It is accordingly a general object of the present invention to provide an improved surgical suture.

Another object of this invention is to provide an improved surgical suture that has a porous surface, coating or layer external thereof.

Another object of the present invention is to provide an improved surgical suture that is of the non-braided, non-woven type, while still having compressible qualities for reducing blood leakage at suture sites in vascular anastomoses.

Another object of the present invention is to provide an improved surgical suture that permits body tissue ingrowth into an external portion thereof that provides a porous surface.

Another object of this invention is to provide an improved porous surgical suture for accelerating the healing process and for reducing the likelihood of primary or secondary infection.

Another object of the present invention is to provide an improved surgical suture that can be made from the same material and can be provided with the same surface structure as a synthetic graft or the like that is being fixed in place by the suture.

Another object of this invention is to provide an improved surgical suture that is provided with surface irregularities that lessen the likelihood of slippage when the suture is tied and that provide a favored environment for the controlled release of drugs to promote healing and/or to resist infection.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 6 is a generally schematic sketch showing a step in the manufacture of the porous suture in accordance with FIG. 1;

FIG. 7 is a broken away elevational view of another embodiment of the porous suture in accordance with this invention;

FIG. 8 is a cross-sectional view along the line 8—8 of FIG. 7;

FIG. 9 is an illustration of the porous surface of the embodiment of FIGS. 7 and 10;

FIG. 10 is an elevational view, partially broken away, of a further embodiment in accordance with this invention;

FIG. 11 is a cross-sectional view along the line 11—11 of FIG. 10;

FIG. 12 is a sketch of a detailed and enlarged view of the preferred porous suture according to this invention; and FIG. 13 is a sketch of an edge of the porous suture sketch of FIG. 12.

DESCRIPTION OF THE PARTICULAR EMBODIMENTS

Figure 1:
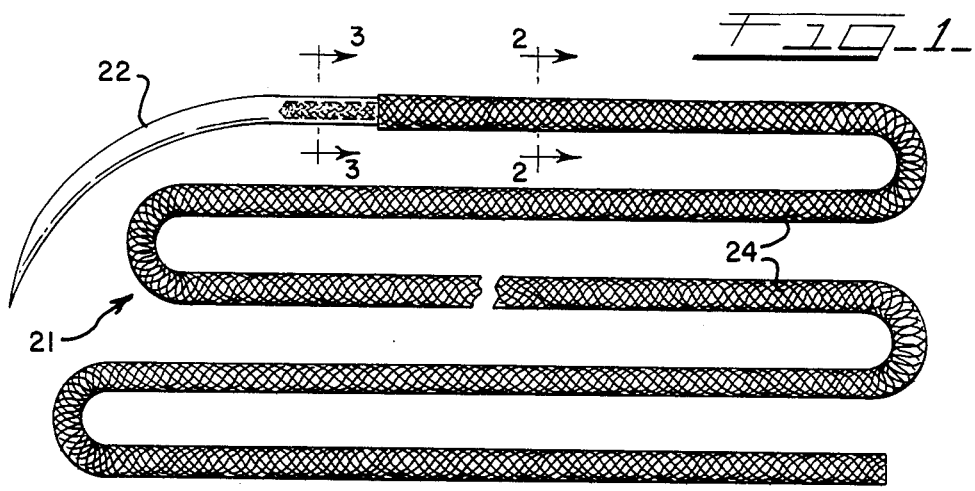
FIG. 1 is an elevational view of a porous suture in accordance with this invention.

An assembly of a length of suture material, generally designated as 21, and a suture needle 22 is illustrated in FIG. 1. Needle 22 is attached to the suture material 21 by crimping, swaging or the like. Preferably, the suture needle 22 has an outside diameter that is smaller than the uncompressed outside diameter of the suture material 21 in order to assist in reducing or preventing leakage along the suture line during and after surgery, this feature being possible in large measure due to the radial compressibility of the suture material 21.

With more particular reference to the suture material that is illustrated in FIGS. 2, 3, 4, 5, 12 and 13, such includes a central core 23 and a generally cylindrical porous elongated portion 24 or 24a which is in the form of a generally cylindrical elongated porous polymeric surface or sheath that has an inside diameter which is substantially the same as the outside diameter of the central core 23 so that the porous portion or layer 24 or 24a closely overlies and is substantially attached to the central core 23 by virtue of a close-fitting relationship or by heat or solvent bonding.

Figure 2:
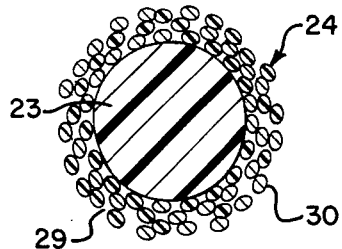
FIG. 2 is a cross-section along the line 2—2 of FIG. 1.
Figure 3:
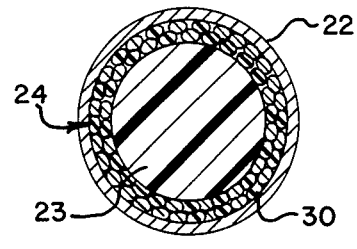
FIG. 3 is a cross-section along the line 3—3 of FIG. 1.

Central core 23 may be a monofilament as illustrated in FIGS. 2 or 3, or same can be composed of a plurality of filaments (not shown). Porous portion or sheath 24 (as illustrated in more detail in FIGS. 12 and 13) and porous portion or sheath 24a (FIGS. 4 and 5) are each composed of a plurality of polymeric fibers that are generally spun onto the central core 23 so as to form pores 29. A suitable spinning technique is illustrated in FIG. 6 in conjunction with an apparatus that extrudes one or more filaments 25 onto a secured central core 23.

Regarding the apparatus illustrated in FIG. 6, such includes a spinnerette or distributor 26 for directing the filaments 25, typically in conjunction with formation of those filaments by extrusion techniques, onto the polymeric central core 23 which is held under tension by suitable jaws 27. In the arrangement illustrated in FIG. 6, the distributor 26 moves back and forth within a plane generally between the jaws 27, while the central core 23 is rotated by suitable means such as the illustrated motors 28. Alternatively, the distributor 26 can take the form of a spinnerette that rotates around the tensioned central core 23. Whatever mechanism or technique is utilized, same will result in combined rotational and translational relative movement between the central core 23 and the filaments 25.

Numerous layers of polymeric fibers can be laid down from the filaments 25 over the central core 23, the number of layers being dependent upon the desired outer diameter size of the suture material 21. On the order of 1000 filament passes can be typical. Sizes of suture material 21 can range between that of a 12-0 U.S.P. size suture having an outer diameter as small as 0.001 mm and a U.S.P. size 2 suture having an outer diameter as large as about 0.599 mm. Thus, suture material 21 may have an outside diameter between about 0.001 mm and about 0.6 and above, depending upon the desired suture use.

Typical sizes of suture material 21 according to this invention include a 7-0 suture material having a diameter of between about 0.050 and 0.069 mm, while the diameter of a 6-0 suture material is on the order of between about 0.070 and 0.099 mm. Each polymeric fiber can have a diameter ranging between about 0.001 to 0.020 mm, typically on the order of about 0.005 mm, in order to form a porous coating 24 or 24a having a thickness between about 0.010 and about 0.200 mm, preferably between about 0.050 and about 0.150 mm. The average size of each pore 29 is on the order of about 0.005 and about 0.060 mm.

In a specific example, 6-0 suture material according to this invention has a polymeric central core 23 having a diameter of between about 0.020 and about 0.049 mm, while the porous polymeric coating 24 or 24a has a thickness of about 0.050 mm, being made up of 0.005 mm polymeric fibers that are laid down in a maximum of about 2000 filament passes to form a porous coating 24 or 24a having the total thickness of about 0.050 mm. The number of revolutions needed to lay down these filament passes depends primarily upon the number of nozzles on the spinnerette or distributor 26. In this example, the spacing between each polymeric fiber is so chosen to provide pores 29 having an average size of approximately 0.025 mm. Such porosity is determined by the diameter of the polymeric fibers, the closeness of these fibers to each other when wound, the number of layers of such polymeric fibers, and the extent that ad3acent ones of such fibers fuse together.

Figure 4:
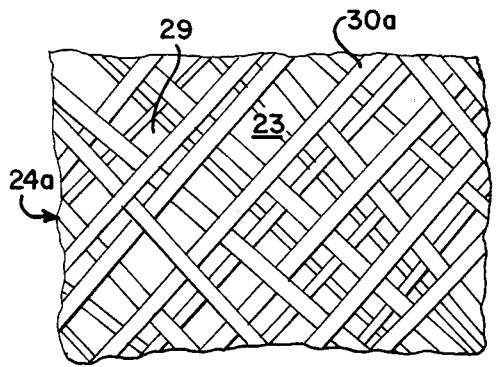
FIG. 4 is a sketch of a porous coating and suture according to the invention at a magnification on the order of 150 times.
Figure 5:
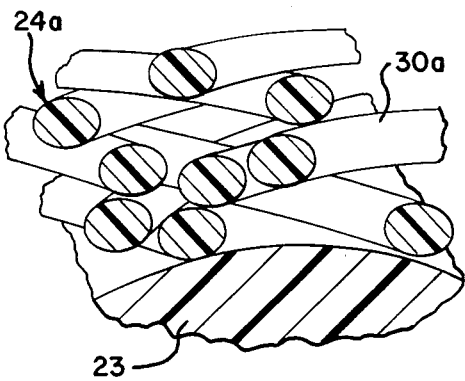
FIG. 5 is a sketch of an edge of the porous suture of FIG. 4 at an approximate magnification of 1000 times.

With specific reference to the embodiment of the porous coating 24a that is illustrated in FIGS. 4 and 5, the filaments 25 are spun so that they are laid down as polymeric fibers 30a onto the core 23 and onto each other in a manner by which each polymeric fiber 30a maintains its generally cylindrical configuration throughout its length. Where the fibers 30a generally cross each other in the FIGS. 4 and 5 embodiment, they only slightly modify their respective generally cylindrical shapes to form the porous coating 24a.

Enhanced strength over that experienced by the suture having a porous coating 24a is imparted to the porous suture by providing the preferred porous coating 24 illustrated in FIGS. 12 and 13. In this preferred embodiment, individual polymeric fibers 30 are laid down when they are in a softened, substantially plastic state, whereby they deform from their respective generally cylindrical configurations, especially at those locations where they cross over or otherwise engage one another. Such deformed polymeric fibers 30 are generally S-shaped along their length and tend to exhibit complementary and oppositely oriented indents at those locations where adjacent fibers 30 cross one another. As a result, each subsequent layer of the fibers 30 generally "sinks" toward the central core 23 and generally drapes over the layer of fibers 30 lying thereunder. The deformability or plasticity needed to thus form these polymeric fibers 30 is typically achieved by extruding the filaments 25 in a manner by which their hardening is delayed, for example by being accompanied by excess or residual solvent.

Other embodiments, such as those illustrated in FIGS. 7, 8, 9, 10 and 11, do not incorporate filaments in this same manner. The porosity of the suture material of those embodiments is determined by the size of elutable particles and the concentration of those particles, as a percent by volume of a pre-elution mixture thereof with the polymer of the suture material. These embodiments incorporate an elution technique for forming a porous suture material 31 or 41 which may, if desired, be attached to a suture needle 32 by crimping or swaging.

In the embodiment illustrated in FIGS. 7, 8 and 9, the suture material 31 includes a central core 33 and porous coating 34. The porous coating 34 is formed by applying, over the central core 33, a mixture of a polymeric material and elutable particles such as salt granules, after which the elutable particles are dissolved out to form a plurality of pores 39. This mixture of polymeric material and elutable particles may be extruded onto the central core 33 by available extrusion devices so that the mixture surrounds and forms a sheath-like surface over the central core 33.

Alternatively, as illustrated in FIGS. 10 and 11, the mixture of polymeric material and elutable particles may be extruded as a solid cylinder. Subsequent elution of this solid cylinder forms the porous suture material 41 which has a central core 43 that is integral with and that is a continuous, unitary portion of the polymeric material that surrounds the central core 43 and that includes eluted pores 49. With this embodiment, there is no need to secure a porous coating to a separate central core by force fitting, heat bonding, adhesive bonding or the like.

Porous suture material 41, in addition to being made of a flexible non-metallic material, including any of various polymeric materials, may be made of carbon and derivatives thereof, other organic substances, and other materials that are either inert or biodegradable. Suitable polymeric materials include polyurethanes, polycarbonates and various copolymers. Polyurethanes are preferred because of their biocompatibility and flexibility. Satisfactory elutable particles include salts such as sodium chloride crystals, sodium carbonate, calcium fluoride, magnesium sulfate and other water-soluble materials that are readily leached by the utilization of water as the elution medium. Other particles that are soluble in organic solvents and the like can be substituted as desired.

In those embodiments that utilize a suture material that is an assembly of a central core and a porous coating, both components of the suture material may be made of the same material, or they may be made of differing materials depending upon the particular objective to be achieved. For example, there might be a desire to have the porous coating constructed of the same material as the prosthetic device or graft that is to be sutured by the suture material, while it might be desirable to provide a central core of that same suture material which is especially flexible or which has a particularly high tensile strength or which possesses some other highly desirable property for a particular use.

It will be understood that the embodiments of the present invention which have been described are illustrative of some of the applications of the principles of the present invention. Numerous modifications may be made by those skilled in the art without departing from the true spirit and scope of the invention.

I claim:

1. A non-braided surgical suture, comprising:
   a suture material including:
   a flexible, non-metallic elongated central core member having an outside diameter that is less than that of the non-braided surgical suture;
   a generally cylindrical porous elongated flexible, non-metallic portion that has an inside diameter which is substantially the same as said central core member outside diameter and that has an outside diameter that is no larger than that of a surgical suture, said generally cylindrical porous elongated flexible portion closely overlying said elongated central core member, and said generally cylindrical porous elongated flexible portion having a porous surface that promotes tissue ingrowth into said porous elongated flexible portion; and
   said generally cylindrical elongated flexible portion includes a spun filament that is wound onto the elongated central core member into multiple layers that cross each other in order to form said porous surface.

2. The non-braided surgical suture according to claim 1, wherein said generally cylindrical porous elongated flexible coating is a polymeric sheath that is secured to the central core member.

3. The non-braided surgical suture according to claim 1, wherein the flexible elongated central core member is a single-strand polymeric extrudate of said filament spun into said multiple layers.

4. The non-braided surgical suture according to claim 1, wherein the flexible elongated central core member is a multiple-strand polymeric extrudate of said filament spun into said multiple layers.

5. The non-braided surgical suture according to claim 1, wherein said generally cylindrical porous elongated flexible portion includes a plurality of fibers of said spun filament that are wound onto said flexible elongated central core member to form said multiple layers.

6. The non-braided surgical suture according to claim 1, wherein said generally cylindrical porous elongated flexible portion includes a plurality of fibers of said spun filament that are wound onto the elongated central core member into said multiple layers.

7. The non-braided surgical suture according to claim 1, wherein said generally cylindrical elongated flexible portion is a porous sheath that includes a plurality of said multiple layers of spun filament that are heat bonded to each other.

8. The non-braided surgical suture according to claim 1, wherein said generally cylindrical elongated flexible portion is a porous sheath that includes a plurality of said multiple layers of spun filament that are solvent bonded to each other.

9. The non-braided surgical suture according to claim 1, further including a needle member attached to a radially compressed end portion of said suture material.

10. The non-braided surgical suture according to claim 10, wherein said needle member has an outside diameter that is smaller than said outside diameter of said generally cylindrical porous elongated flexible portion that is radially uncompressed.

11. The non-braided surgical suture according to claim 1, wherein said outside diameter of said generally cylindrical porous elongated flexible portion has a diameter of between about 0.001 and about 0.6 mm and above.

12. The non-braided surgical suture according to claim 1, wherein said porous surface has a pore size of on the order of about 0.005 and about 0.06 mm.

13. The non-braided surgical suture according to claim 1, wherein said suture material is made of polymers that are polyurethanes.

* * * * *